United States Patent
Zappacosta et al.

(10) Patent No.: US 9,980,756 B2
(45) Date of Patent: May 29, 2018

(54) DEVICE AND A METHOD FOR IMPLANTING A SPINOUS PROCESS FIXATION DEVICE

(71) Applicant: GLOBUS MEDICAL, INC., Audubon, PA (US)

(72) Inventors: Jason Zappacosta, Philadelphia, PA (US); Robert Rightler, Pennsburg, PA (US); Christopher Angelucci, Schwenksville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days. days.

(21) Appl. No.: 15/290,163

(22) Filed: Oct. 11, 2016

(65) Prior Publication Data

US 2017/0027622 A1   Feb. 2, 2017

Related U.S. Application Data

(63) Continuation of application No. 14/286,625, filed on May 23, 2014, now Pat. No. 9,486,254, which is a continuation of application No. 13/466,228, filed on May 8, 2012, now Pat. No. 8,771,277.

(51) Int. Cl.
*A61B 17/70* (2006.01)
*A61B 17/88* (2006.01)
*A61B 17/56* (2006.01)

(52) U.S. Cl.
CPC ...... *A61B 17/7074* (2013.01); *A61B 17/7068* (2013.01); *A61B 2017/564* (2013.01)

(58) Field of Classification Search
CPC ............ A61B 17/7074; A61B 17/7068; A61B 2017/564
USPC .................. 606/246–249, 86 A, 280, 71, 99; 623/17.11, 17.16
See application file for complete search history.

(56) References Cited

U.S. PATENT DOCUMENTS

| | | |
|---|---|---|
| 3,056,852 A | 10/1962 | Sachs |
| 3,426,364 A | 2/1969 | Lumb |
| 4,116,104 A | 9/1978 | Kennedy |
| 4,349,921 A | 9/1982 | Kuntz |
| 4,863,476 A | 9/1989 | Shepperd |
| 4,863,477 A | 9/1989 | Monson |
| 5,390,683 A | 2/1995 | Pisharodi |
| 5,496,318 A | 3/1996 | Howland |
| 5,645,596 A | 7/1997 | Kim et al. |
| 5,665,122 A | 9/1997 | Kambin |
| 5,860,977 A | 1/1999 | Zucherman |
| 6,039,761 A | 3/2000 | Li |

(Continued)

FOREIGN PATENT DOCUMENTS

| | | |
|---|---|---|
| WO | 2006045094 A2 | 4/2006 |
| WO | 2006113080 A2 | 10/2006 |

(Continued)

*Primary Examiner* — Pedro Philogene
*Assistant Examiner* — David C Comstock

(57) ABSTRACT

The disclosure provides a device to facilitate the insertion and attachment of an implant that includes a barrel assembly and a plate assembly in an interspinous space. The device comprises a main body, a first arm that is configured to hold the barrel assembly, and a second arm that is configured to hold a locking plate of the plate assembly, wherein the first and second arms are movably attached to the main body.

18 Claims, 9 Drawing Sheets

(56) References Cited

U.S. PATENT DOCUMENTS

| | | |
|---|---|---|
| 6,045,579 A | 4/2000 | Hochshuler et al. |
| 6,068,630 A | 5/2000 | Zucherman |
| 6,080,193 A | 6/2000 | Hochshuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,312,431 B1 | 11/2001 | Asfora |
| 6,364,883 B1 | 4/2002 | Santilli |
| 6,419,676 B1 | 7/2002 | Zucherman |
| 6,451,019 B1 | 9/2002 | Zucherman |
| 6,554,863 B2 | 4/2003 | Paul et al. |
| 6,562,074 B2 | 5/2003 | Gerbec |
| 6,576,016 B1 | 6/2003 | Hochshuler et al. |
| 6,641,614 B1 | 11/2003 | Wagner et al. |
| 6,648,917 B2 | 11/2003 | Gerbec |
| 6,652,527 B2 | 11/2003 | Zucherman |
| 6,666,891 B2 | 12/2003 | Boehm, Jr. et al. |
| 6,692,495 B1 | 2/2004 | Zacouto |
| 6,695,842 B2 | 2/2004 | Zucherman |
| 6,706,070 B1 | 3/2004 | Wagner et al. |
| 6,752,832 B2 | 6/2004 | Neumann |
| 6,830,589 B2 | 12/2004 | Erickson |
| 6,849,093 B2 | 2/2005 | Michelson |
| 6,852,129 B2 | 2/2005 | Gerbec |
| 6,863,673 B2 | 3/2005 | Gerbec |
| 6,881,228 B2 | 4/2005 | Zdeblick |
| 7,018,415 B1 | 3/2006 | Mckay |
| 7,048,736 B2 | 5/2006 | Robinson |
| 7,201,751 B2 | 4/2007 | Zucherman |
| 7,217,291 B2 | 5/2007 | Zucherman |
| 7,282,063 B2 | 10/2007 | Cohen et al. |
| 7,335,203 B2 | 2/2008 | Winslow |
| 7,476,251 B2 | 1/2009 | Zucherman |
| 7,547,325 B2 | 6/2009 | Biedermann et al. |
| 7,621,953 B2 | 11/2009 | Braddock, Jr. |
| 7,641,693 B2 | 1/2010 | Gütlin |
| 7,682,396 B2 | 3/2010 | Beaurain |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | Mckinley |
| 7,815,683 B2 | 10/2010 | Melkent |
| 7,828,849 B2 | 11/2010 | Lim |
| 7,837,734 B2 | 11/2010 | Zucherman |
| 7,875,078 B2 | 1/2011 | Wysocki |
| 8,114,132 B2 | 2/2012 | Lyons |
| 8,206,420 B2 | 6/2012 | Patel |
| 8,357,181 B2 | 1/2013 | Lange |
| 8,382,842 B2 | 2/2013 | Greenhalgh |
| 8,435,298 B2 | 5/2013 | Weiman |
| 2002/0045945 A1 | 4/2002 | Liu |
| 2002/0091446 A1 | 7/2002 | Zucherman |
| 2003/0040746 A1 | 2/2003 | Mitchell |
| 2003/0216736 A1 | 11/2003 | Robinson |
| 2004/0049271 A1 | 3/2004 | Biedermann et al. |
| 2004/0153065 A1 | 8/2004 | Lim |
| 2005/0033432 A1 | 2/2005 | Gordon |
| 2005/0149188 A1 | 7/2005 | Cook et al. |
| 2005/0171541 A1 | 8/2005 | Boehm, Jr. |
| 2005/0273171 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0058878 A1 | 3/2006 | Michelson |
| 2006/0122701 A1 | 6/2006 | Kiester |
| 2006/0129244 A1 | 6/2006 | Ensign |
| 2006/0149385 A1 | 7/2006 | Mckay |
| 2006/0195192 A1 | 8/2006 | Gordon |
| 2006/0229729 A1 | 10/2006 | Gordon |
| 2006/0247640 A1 | 11/2006 | Blackwell |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings |
| 2007/0055377 A1 | 3/2007 | Hanson |
| 2007/0162001 A1 | 7/2007 | Chin |
| 2007/0179500 A1 | 8/2007 | Chin |
| 2007/0191951 A1 | 8/2007 | Branch, Jr. |
| 2007/0233082 A1 | 10/2007 | Chin |
| 2007/0270812 A1 | 11/2007 | Peckham |
| 2007/0270840 A1 | 11/2007 | Chin |
| 2008/0021471 A1 | 1/2008 | Winslow |
| 2008/0021472 A1 | 1/2008 | Winslow |
| 2008/0021559 A1 | 1/2008 | Thramann |
| 2008/0065222 A1 | 3/2008 | Hamada |
| 2008/0140207 A1 | 6/2008 | Olmos |
| 2008/0167657 A1 | 7/2008 | Greenhalgh |
| 2008/0183204 A1 | 7/2008 | Greenhalgh |
| 2008/0183211 A1 | 7/2008 | Lamborne |
| 2008/0281346 A1 | 11/2008 | Greenhalgh |
| 2008/0281359 A1 | 11/2008 | Abdou |
| 2008/0288073 A1 | 11/2008 | Renganath |
| 2008/0300598 A1 | 12/2008 | Barreiro et al. |
| 2008/0319549 A1 | 12/2008 | Greenhalgh |
| 2009/0024217 A1 | 1/2009 | Levy et al. |
| 2009/0062918 A1 | 3/2009 | Wang et al. |
| 2009/0125062 A1 | 5/2009 | Arnin |
| 2009/0149956 A1 | 6/2009 | Greenhalgh |
| 2009/0149959 A1 | 6/2009 | Conner |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner |
| 2009/0281628 A1 | 11/2009 | Oglaza |
| 2009/0292361 A1 | 11/2009 | Lopez |
| 2009/0299478 A1 | 12/2009 | Carls |
| 2010/0049324 A1 | 2/2010 | Valdevit |
| 2010/0070041 A1 | 3/2010 | Peterman |
| 2010/0082109 A1 | 4/2010 | Greenhalgh |
| 2010/0087860 A1 | 4/2010 | Chin et al. |
| 2010/0179657 A1 | 7/2010 | Greenhalgh |
| 2010/0185291 A1 | 7/2010 | Jimenez |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222884 A1 | 9/2010 | Greenhalgh |
| 2010/0234952 A1 | 9/2010 | Peterman |
| 2010/0249933 A1 | 9/2010 | Trieu |
| 2010/0280622 A1 | 11/2010 | Mckinley |
| 2010/0286779 A1 | 11/2010 | Thibodeau |
| 2010/0286780 A1 | 11/2010 | Dryer |
| 2010/0292796 A1 | 11/2010 | Greenhalgh |
| 2010/0305705 A1 | 12/2010 | Butler |
| 2010/0331981 A1 | 12/2010 | Mohammed |
| 2010/0331985 A1 | 12/2010 | Gordon |
| 2011/0022090 A1 | 1/2011 | Gordon |
| 2011/0035011 A1 | 2/2011 | Cain |
| 2011/0066186 A1* | 3/2011 | Boyer, II ............ A61B 17/7065 606/249 |
| 2011/0093074 A1 | 4/2011 | Glerum |
| 2011/0144692 A1 | 6/2011 | Saladin |
| 2011/0184468 A1 | 7/2011 | Metcalf, Jr. |
| 2011/0224731 A1 | 9/2011 | Smisson, III et al. |
| 2011/0319936 A1 | 12/2011 | Gordon et al. |
| 2012/0221050 A1* | 8/2012 | Ingalhalikar ....... A61B 17/7068 606/248 |
| 2013/0012996 A1 | 1/2013 | Zamani et al. |
| 2013/0184751 A1* | 7/2013 | Siegfried ............ A61B 17/7068 606/248 |

FOREIGN PATENT DOCUMENTS

| | | |
|---|---|---|
| WO | 2008044057 A1 | 4/2008 |
| WO | 2011031924 A2 | 3/2011 |

* cited by examiner

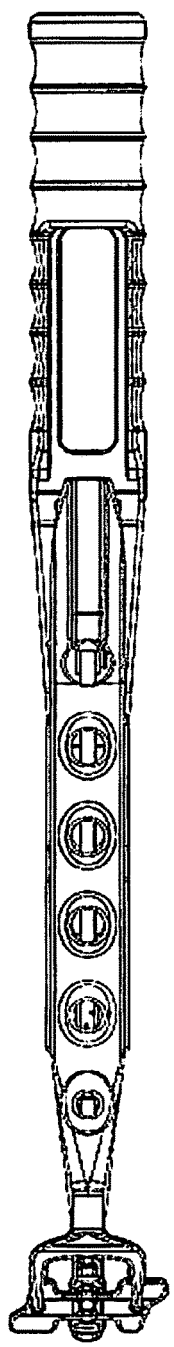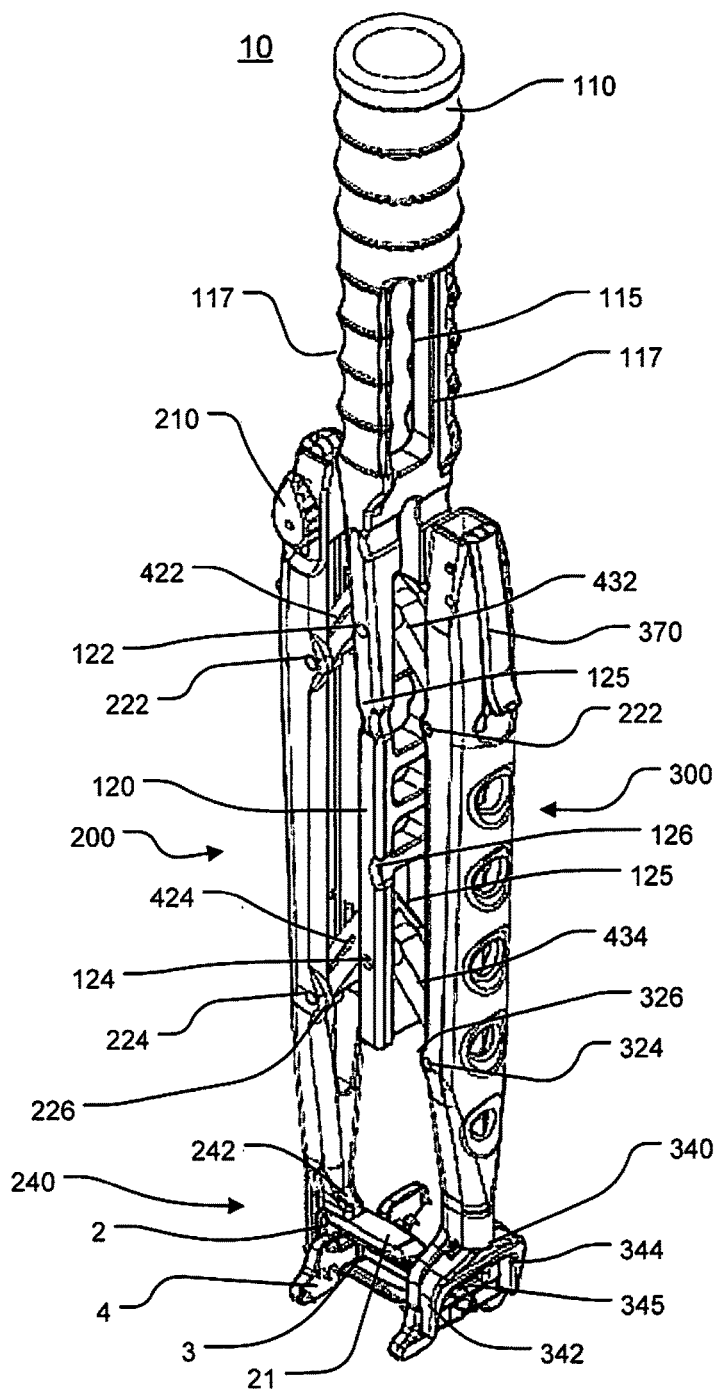
Fig. 3C
Fig. 3D

DEVICE AND A METHOD FOR IMPLANTING A SPINOUS PROCESS FIXATION DEVICE

CROSS REFERENCE TO RELATED APPLICATIONS

This application is a continuation of U.S. patent application Ser. No. 14/286,625, filed May 23, 2014, which is a continuation of U.S. patent application Ser. No. 13/466,228, filed May 8, 2012, now issued as U.S. Pat. No. 8,771,277, which are each incorporated in their entirety herein.

BACKGROUND OF THE PRESENT DISCLOSURE

1. Field of the Present Disclosure

The present disclosure is generally directed to a surgical device that may be used to, e.g., insert and attach (or remove and extract) a spinous process fixation device.

2. Related Art

A spine comprises vertebrae which are a series of small bones, and also includes spinous processes. A spinous process is one of two bony protrusions arising from the posterior side of each vertebra in the human spine. Extending backwards and downwards from the main body of the vertebra, each spinous process is an extension of the lamina. The laminae are two bony plates that converge at the back of each vertebra to form the vertebral arch. The spinous processes curve outward from this junction. A variety of scenarios may exist where damage to the spine may occur including, but not limited to, injury or illness. Severe, even debilitating, pain can result from such damage. In some instances, artificial assistance may be necessary to address such damage.

Surgical procedures exist that attempt to address such damage including using various vertebral fixation devices. Conventional devices exist to implant vertebrae fixation devices, but such devices often suffer from the problem of being purely manual and are usually complex. Such manual devices require the use of human muscle, which can fatigue, to perform the procedure. Moreover, the incision opening for insertion of these fixation devices may require substantial openings to achieve access to the spinous process.

Accordingly, there is a need for a surgical device that improves and simplifies a surgeon's ability to insert (or remove) a spinous process fixation device in (from) a patient.

SUMMARY OF THE PRESENT DISCLOSURE

The present disclosure meets the foregoing need of improving and simplifying a surgeon's ability to insert (or remove) a spinous process fixation device. The surgical device, according to the present disclosure, comprises a posterior, non-pedicle supplemental fixation device that may be implemented, for example, to insert and attach (or remove and extract) a fixation device in a non-cervical spine. During implementation, the surgical device preserves a supraspinous ligament, attaching firmly to the spinous processes above and below an interspinous space. The fixation device is constructed to withstand the compressive, torsional, and shear loads that can be found in the lumbar spine.

Accordingly, one aspect of the present disclosure provides a device to facilitate the insertion and attachment of an implant that includes a barrel assembly and a plate assembly in an interspinous space. The device comprises a main body, a first arm that is configured to hold the barrel assembly, and a second arm that is configured to hold a locking plate of the plate assembly, wherein the first and second arms are movably attached to the main body.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings:

FIGS. 3A-3D correspond to FIGS. 2A-2D, except that the surgical device is configured in a second operable position;

DETAILED DESCRIPTION OF THE PRESENT DISCLOSURE

Figure 1A:
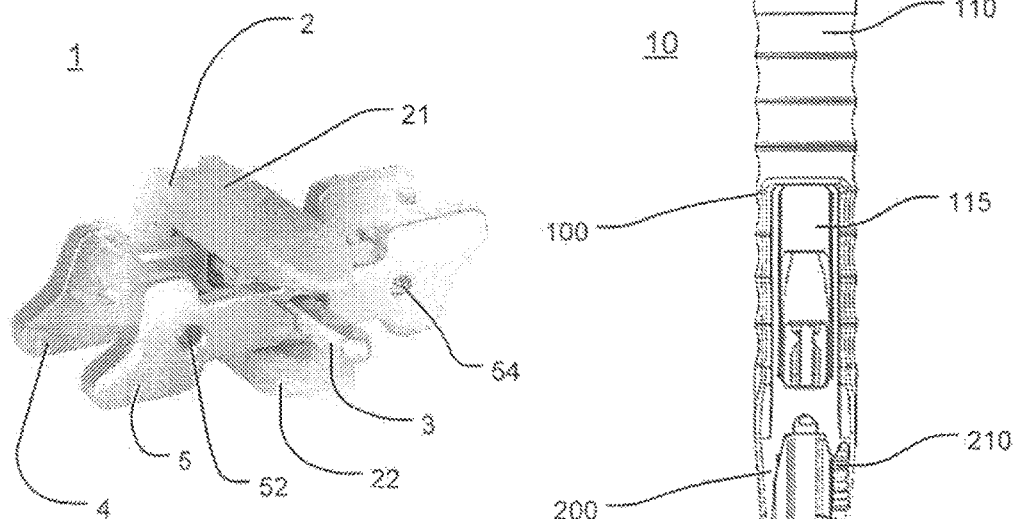
FIG. 1A shows an example of a spinous process fixation device that may be used with a surgical device that is constructed according to the principles of the disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The present disclosure is generally directed to a surgical device. More specifically, the disclosure may be directed to a device, used by a surgeon, to facilitate the insertion and attachment (or removal and extraction) of a spinous process fixation device above and below an interspinous space, while preserving the supraspinous ligament. The spinous process fixation device (or implant) may comprise, but is not limited to, for example, a SP-FIX™ spinous process fixation system, which is manufactured by Globus Medical, Inc., or similar devices.

The word "surgeon," as used in this disclosure, means any person that uses the disclosure to either sever tissue or attempt to sever tissue. Such a person may be educated, certified, and trained to perform surgical procedures involving the removal of tissue. Such a person may also be a lay person with no experience in the surgical field. In addition, such a person may have a skill-set, education, and/or knowledge base which falls somewhere between a person who may be educated, certified, and trained to perform surgical procedures and a lay person.

Surgical intervention for back pain is usually reserved for people with chronic back pain, perhaps for which other treatments have failed. Surgery may be required for people who have, for example, chronic lower back pain and sciatica (often diagnosed with a herniated disc), spinal stenosis, spondylolisthesis (vertebra of the lumbar spine slips out of place), or vertebral fractures with nerve involvement. Also, surgery may be necessary for people with discogenic lower back pain (e.g., degenerative disc disease) that may occur as part of the aging process. In these situations, among others, implants may be included in a course of treatment. Generally, the goal may be to achieve supplemental fusion.

FIG. 1A shows an example of an implant 1 that may be used with a surgical device that is constructed according to the principles of the disclosure. The implant 1 may comprise a barrel assembly 2, 3, and a plate assembly 4, 5. The barrel assembly 2, 3 may include a barrel body 2 and an integrated central ratcheting rod 3. The barrel body may include a pair of extensions 21, 22 that form a mouth 23 of the barrel body 2 at one end. The barrel body 2 may include a pair of pockets 24 at an end of the pair of extensions 21, 22 that is opposite the mouth 23. The central ratcheting rod 3 may be inserted through the end opposite the mouth 23 and positioned between the extensions 21, 22. The plate assembly may include a pivoting plate 4 and a locking plate 5. The locking plate 5 may include a pair of support openings 52, 54.

Figure 1B:
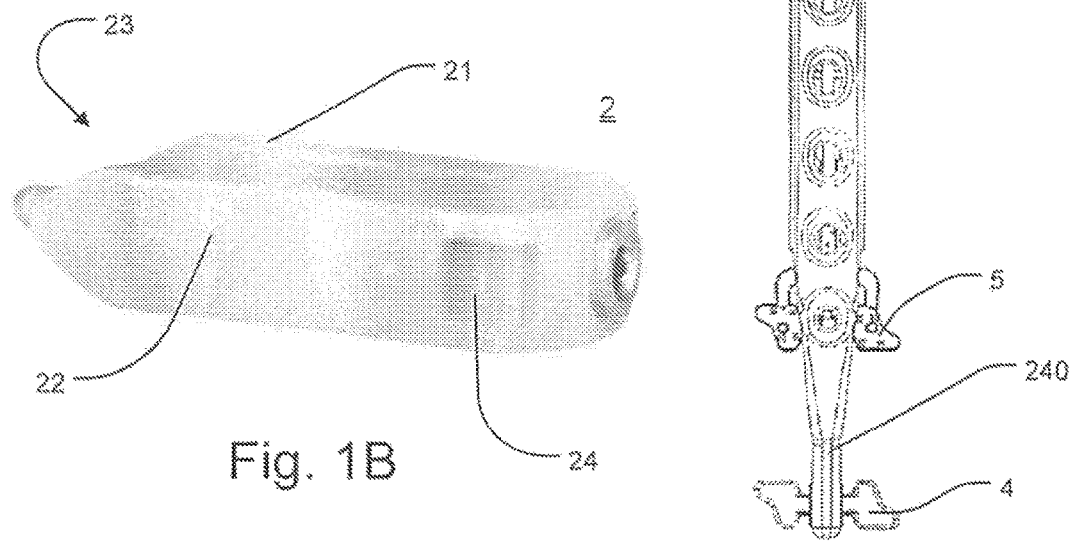
FIG. 1B shows a perspective view of a barrel assembly of the spinous process fixation device of FIG. 1A.

FIG. 1B shows a perspective view of the barrel assembly 2, 3 of the implant 1.

Figure 2A:
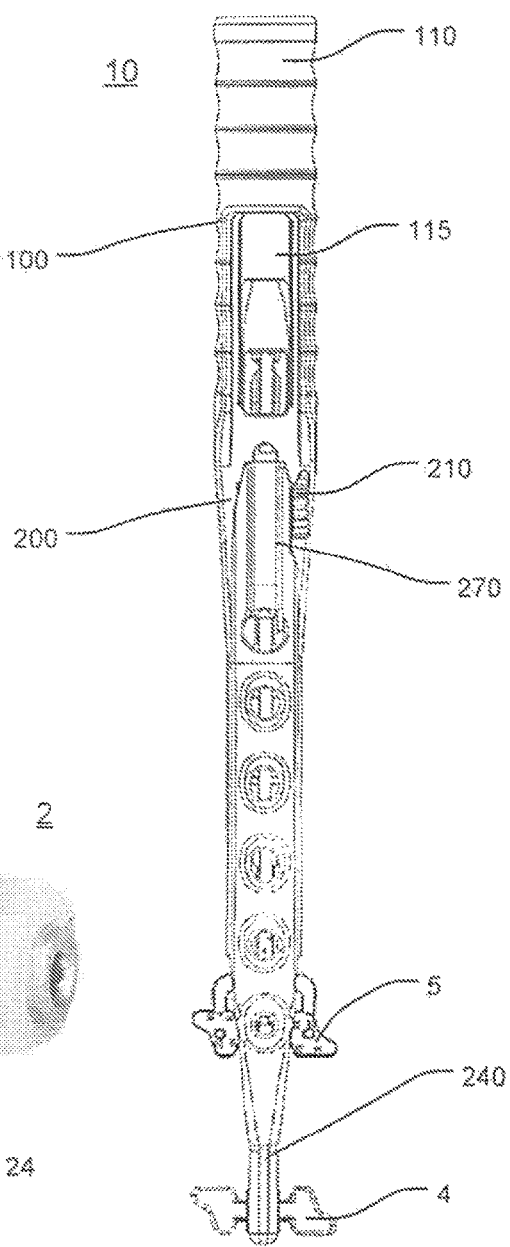
FIG. 2A shows a front view of an example of the surgical device in a first operable position.
Figure 4A:
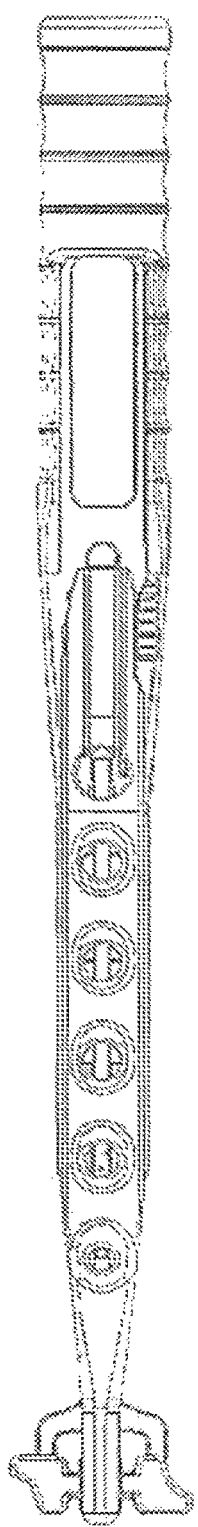
FIGS. 4A-4D correspond to FIGS. 2A-2D, except the surgical device is configured in a third operable position.
Figure 4B:
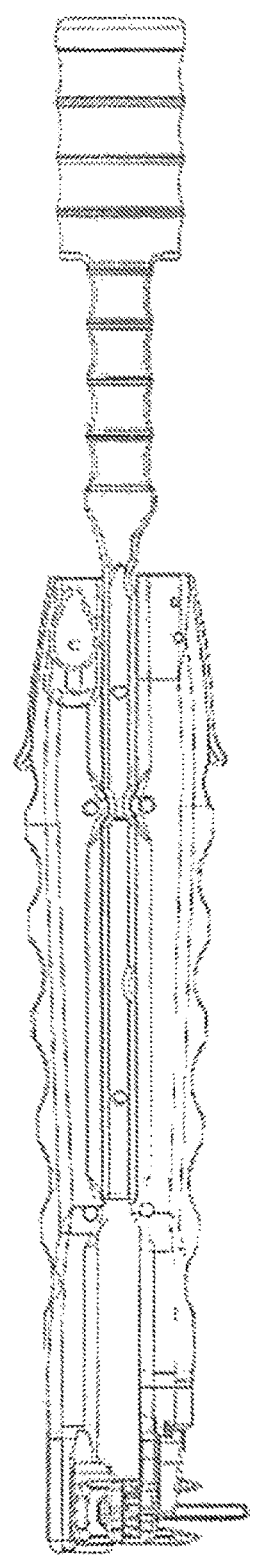
Figure 4C:
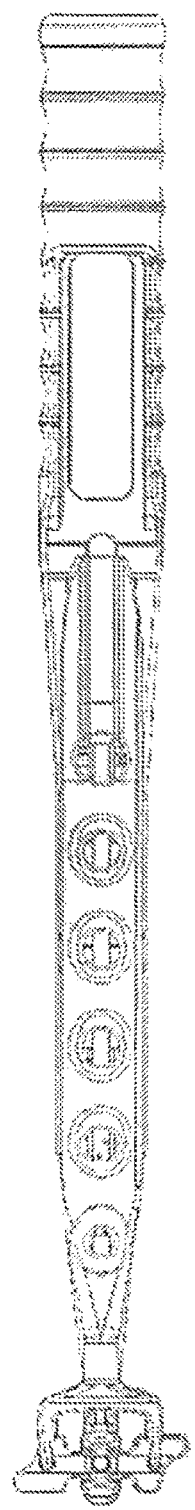
Figure 4D:
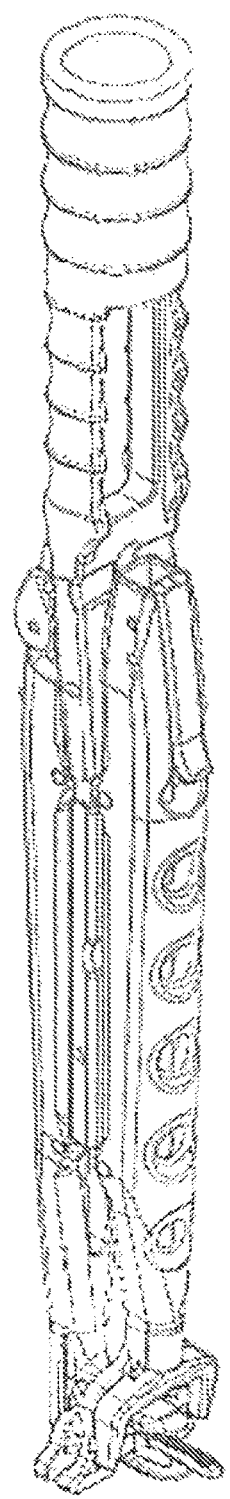
Figure 5A:
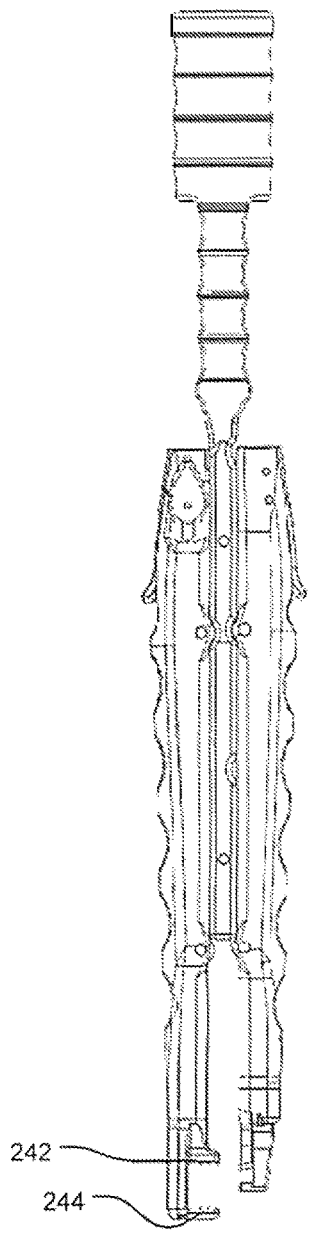
FIG. 5A shows the surgical device in the fourth operable position, without an implant.
Figure 5B:
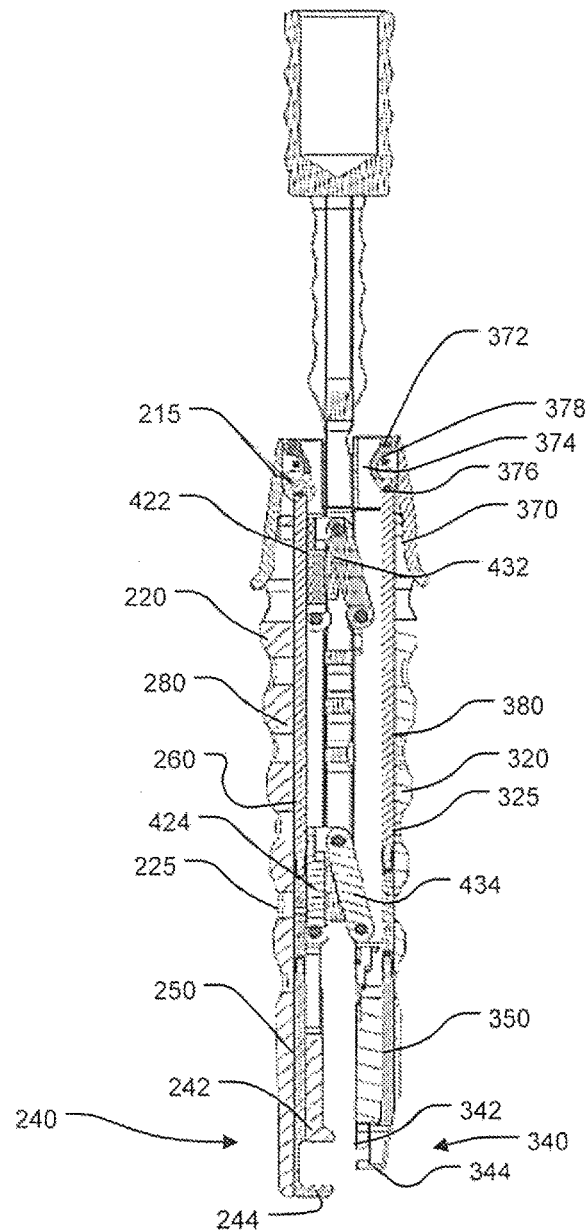
FIG. 5B shows a cross-section cut view of the surgical device of FIG. 5A.
Figure 5C:
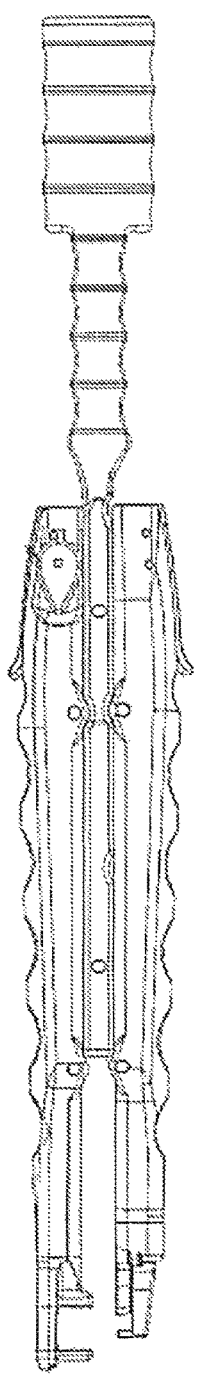
FIG. 5C shows the surgical device in the fourth operable position, after an actuator is adjusted.
Figure 5D:
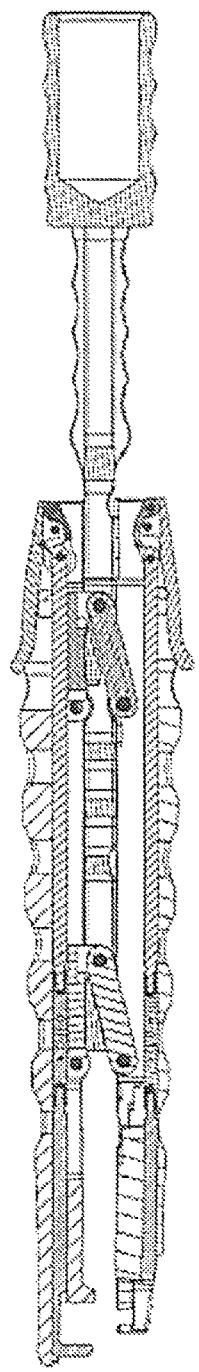
FIG. 5D shows a cross-section cut view of the surgical device of FIG. 5C, taken along a vertical axis, showing internal mechanisms.
Figure 6A:
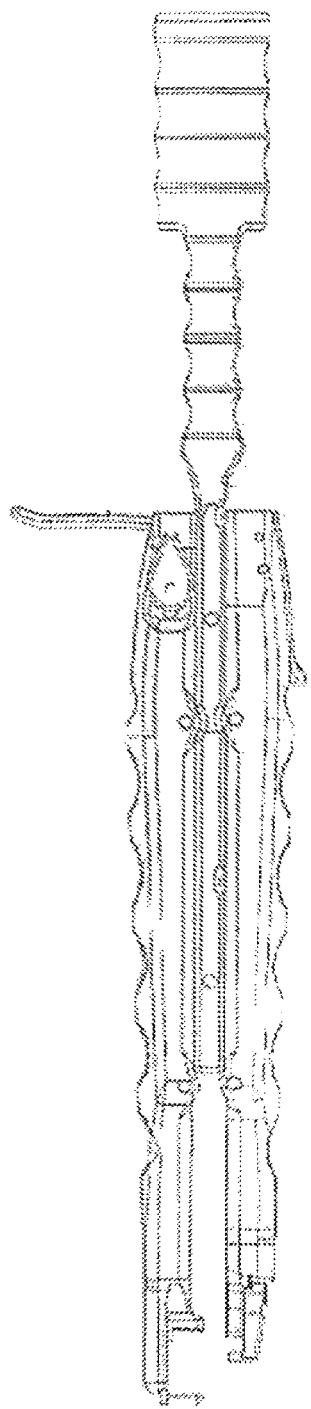
FIG. 6A shows the surgical device in the third operable position, after a release lever is opened.
Figure 6B:
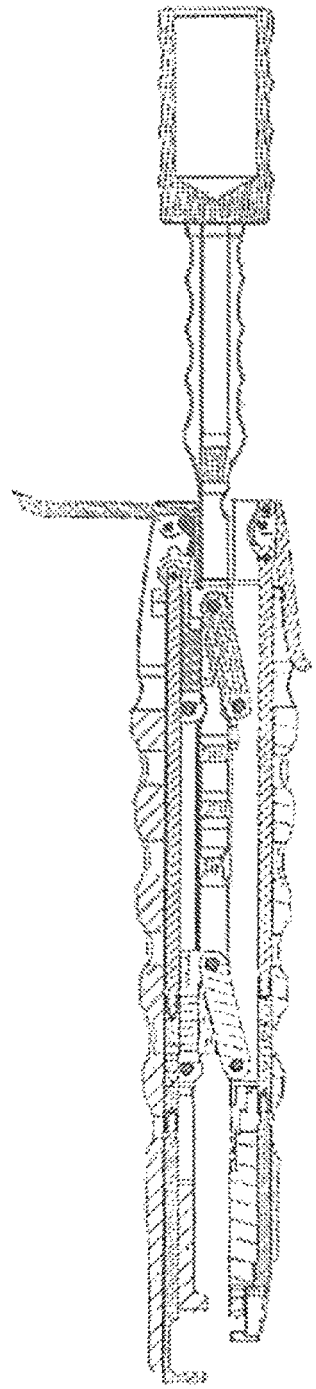
FIG. 6B shows a cross-section cut view of the surgical device of FIG. 6A.

FIGS. 2A-6B show various views of an example of a surgical device 10 in a first operable position, constructed according to the principles of the disclosure. In particular, FIG. 2A shows a front view of the surgical device 10 in a first operable position; FIG. 2B shows a side view of the surgical device 10; FIG. 2C shows a rear view of the surgical device 10; FIG. 2D shows a perspective side view of the surgical device 10; FIGS. 3A-3D correspond to FIGS. 2A-2D, except that the surgical device 10 is configured in a second operable position; FIGS. 4A-4D correspond to FIGS. 2A-2D, except the surgical device 10 is configured in a fourth operable position; FIG. 5A shows the surgical device 10 in the third operable position, without an implant; FIG. 5B shows a cross-section cut view of the surgical device 10 of FIG. 5A; FIG. 5C shows the surgical device 10 in the third operable position, after an actuator is adjusted; FIG. 5D shows a cross-section cut view of the surgical device 10 of FIG. 5C, taken along a vertical axis, showing internal mechanisms; FIG. 6A shows the surgical device 10 in the third operable position, after a release lever is opened; and FIG. 6B shows a cross-section cut view of the surgical device 10 of FIG. 6A. The surgical device 10 is configured as a single instrument that may be used to insert (or extract) and attach an implant firmly to the spinous processes above and below an interspinous space, while immobilizing a lumbar motion segment posteriorly.

Referring to FIG. 3D, the surgical device 10 consists of a single instrument that comprises a main body 100 and a pair of arms 200, 300. The main body 100 may include a handle portion 110 and an arm support portion 120.

The handle portion 110 is configured to be easily grasped and held by, for example, at least one hand. The handle portion 110 may have a substantially cylindrical shape. The handle portion 110 may be ergonomically designed for better fit and comfort in a surgeon's hand. The handle portion 110 may include an opening 115 to reduce the weight of the overall surgical device 10, as well as to allow the surgeon to see through the surgical device 10 during operation. The opening 115 may also be used for storage, allowing the surgical device 10 to be placed, for example, on a tool support (not shown) through the opening 115. The handle portion 110 may further include a pair of cutaway portions 117, each of which is configured to receive an upper portion of the arms 200, 300, thereby providing a compact, portable, and secure overall configuration of the surgical device 10 when, for example, it is not in use. This configuration will also help to keep the arms 200, 300 in proper alignment with each other, as well as with the arm support portion 120.

The arm support portion 120 is configured to movably support the arms 200, 300, allowing each arm to move independently of the other arm. The arm support portion 120 may include a plurality of fasteners 122, 124, each of which may be configured to engage and movably hold an end of a respective cross-arm 422 (432), 424 (434). For example, the fastener 122 may be configured to engage and hold an end of each of the cross-arms 422, 432, the other ends of which may be movably attached to the arms 200, 300, respectively. Similarly, the fastener 124 may be configured to engage and hold an end of each of the cross-arms 424, 434, the other ends of which may be movably attached to the arms 200, 300, respectively. The fasteners 122, 124 may include, but are not limited to, for example, a pin, a rod, a screw, a bolt, a rivet, a nut, a c-clip, a u-clip, a clip, a washer, or the like.

The arm support portion 120 may include one or more cavities 125 that are designed to receive the cross-members 422, 432, 424, 434, so that the arm support portion 120 and arms 200, 300 may be compacted to a configuration of the surgical device 10 that has minimal dimensions when it is in a closed position (e.g., shown in FIGS. 4B and 4D). The cavities 125 may also serve to reduce the overall weight and/or cost of the surgical device 10, as less material may be used to manufacture the arm support portions 120.

The arm support portion 120 may further include a plurality of recesses 126, each of which is configured to receive a corresponding projection 226 or projection 326. When the surgical device 10 is in its fully compacted configuration (not shown), the projections 226, 326 align with and engage corresponding recesses 126 to provide a very compact overall size for the arm support portion 120, which ensures secure alignment of the arms 200, 300 and arm support portion 120 for longevity and optimal performance.

The arm 200 may comprise an actuator 210, an arm body 220, an implement holder 240, and a release lever 270. The actuator 210 may include, but is not limited to, a dial, a lever, a knob, a screw, a bolt, a wing-nut, or the like. The actuator 210 may further include, for example, a cam. The arm body 220 may include a plurality of openings 225 and a channel 280 (shown in FIG. 5B).

Referring to FIG. 5B, the actuator 210 may be operationally coupled to one end of a longitudinal grip member 250. The actuator 210 may be further coupled to a longitudinal guide member 260. The longitudinal grip member 250 and the longitudinal guide member 260 may be located in the channel (or recess) 280 provided in the arm body 220. The longitudinal grip member 250 may include a gripper 244 at the end opposite the end proximal to the actuator 210. The gripper 244 makes up a portion of the holder 240.

In the example shown in FIG. 5B, the actuator 210 comprises a dial that is attached to a cam 215, so that when the dial is manipulated, the cam 215 rotates, forcing the longitudinal grip member 250 to move (e.g., up/down) along the longitudinal axis of the arm 200, thereby driving the gripper 244 to move (e.g., up/down) along the longitudinal axis of the arm 200. The actuator 210 and the longitudinal grip member 250 may be operationally attached to the longitudinal member 260, which may be attached to the release lever 270, such that when the release lever 270 is operated, the entire gripper assembly moves (e.g., up/down) along the longitudinal axis. The gripper assembly may include the actuator 210, the longitudinal grip member 250, and the gripper 244.

The holder 240 comprises the gripper 244 and an associated gripper 242. The associated gripper 242 may be integrally formed with the arm body 220, or provided as a separate component (not shown) that may be securely affixed to the arm body 220.

The release lever 270 may be attached to the arm body 220 and/or the gripper assembly. The release member 270 may be configured to drive the gripper assembly to cause the gripper 244 to move (e.g., up/down) along the longitudinal axis of the arm 200. For instance, the release lever 270 may be configured to engage the entire gripper assembly, so as to move the gripper assembly along the longitudinal axis. Referring to FIGS. 5A and 6A, the actuator 210 is shown as being in a first position in FIG. 5A, prior to the release lever 270 being manipulated to release the gripper 244, and in a second position in FIG. 6A, after the release lever 270 is manipulated to cause the gripper 244 to move (e.g., down) along the longitudinal axis, thereby widening the gripping area of the holder 240.

Referring to FIGS. 3D and 5B, the arm 300 may comprise an arm body 320, a holder 340, and a release lever 370. The arm body 320 may include a plurality of openings 325 and a channel 380.

The release lever 370 may be operationally coupled to one end of a longitudinal plate grip member 350. The longitudinal plate grip member 350 may be located in the channel (or recess) 380 provided in the arm body 320. The longitudinal plate grip member 350 may include a plate gripper 344 at the end opposite to the end proximal to the release lever 370. The longitudinal plate grip member 350 may be configured to move (e.g., up/down) along the longitudinal axis of the arm 300, thereby driving the plate gripper 344 to move (e.g., up/down) along the longitudinal axis of the arm 300. The plate gripper 344 makes up a portion of the holder 340. The longitudinal plate grip member 350 may be formed as a single piece, or from multiple pieces that may be assembled into a single piece. The longitudinal plate grip member 350 may be integrally formed with the plate gripper 344.

In the example shown in FIG. 5B, the release lever 370 may be operationally coupled to the longitudinal plate grip member 350 via, for example, a plurality of fasteners 372, 376 and a release member 374. The fasteners 372, 376 may include, but are not limited to, for example, a pin, a rod, a screw, a bolt, a rivet, a nut, a c-clip, a u-clip, a clip, a washer, a weld, or the like. The release member 374 may be made of a strong, resilient material (e.g., a metal, a plastic, or the like) that may bend when pressed by a lever member 378, thereby storing potential energy. When the lever 370 is released (e.g., lifted up), the lever member 378 is retracted, allowing the release member 374 to release the potential energy stored therein, straightening in the process to cause the longitudinal plate grip member 350 and the plate gripper 344 to move (e.g., down) along the longitudinal axis to widen the grip area of the holder 340.

The holder 340 comprises the plate gripper 344 and an associated plate gripper 342. The holder 340 further comprises a pair of plate support members 346, 348 (shown in FIG. 2C), which are configured to be inserted into the support openings 52, 54 of the locking plate 5, to ensure proper alignment of the locking plate 5 with the pivoting plate 4 when the implant is installed. The support members 346, 348 may be integrally formed with, or attached to each end of a u-shape portion 349 of the holder 340. The u-shape portion 349 includes an opening 345 to allow the extension 21 (or 22) of the barrel body 2 to pass there-through during installation of the implant 1. The associated plate gripper 342 may be integrally formed with the arm body 320, or provided as a separate component (not shown) that may be securely affixed to the arm body 320.

The release lever 370 may be attached to the arm body 320, and positioned so that the lever 378 may engage and bend the release member 379 when the lever 370 is engaged (e.g., shown in FIG. 5B), and substantially disengage and allow the release member 347 to cause the longitudinal plate grip member 350 to move (e.g., down) along the longitudinal axis, by, for example, straightening.

Referring to FIGS. 1A and 2A-2D, the arm 200 may be moved (e.g., downward) to its fully deployed (or extended) length along its longitudinal axis with respect to the arm support portion 120. The arm 300 may be kept in (or moved to) its compact position (e.g., shown in FIG. 2B), so as to keep it out of the way while a barrel assembly 2, 3 and pivoting plate 4 are loaded into the holder 240 of the arm 200. The release lever 270 may be released (or disengaged), thereby expanding the width of the grip area of the holder 240—i.e., the distance between the gripper 244 and the associated gripper 242. An end of a barrel assembly 2, 3 (with the pivoting plate 4) of an implant may be positioned in the holder 240 and the release lever 270 may be engaged, causing the gripper 244 to move (e.g., up) along the longitudinal axis of the arm 200 to engage a pocket 24 of the barrel body 2 and drive the other pocket 24 of the barrel body 2 in the same direction against the associated gripper 242, so that the barrel assembly 2, 3 (and pivoting plate 4) is securely nested in the holder 240. The pivoting plate 4 may have been previously loaded into the barely assembly 2, 3 by turning the central ratcheting rod 3 to draw the pivoting assembly completely into the barrel body 2.

Prior to, or after the barrel assembly 2, 3 and pivoting plate 4 are nested in the holder 240, the arm 300 may be moved (e.g., downward) along its longitudinal axis with respect to the arm support portion 120. The arm 200 may be kept in (or moved to) its compact position (not shown), so as to keep it out of the way while a lock plate 5 is loaded into the holder 340 of the arm 300. The release lever 370 may be released (or disengaged), thereby expanding the width of the grip area of the holder 340—i.e., the distance between the plate gripper 344 and the associated plate gripper 342. An end of the locking plate 5 may be positioned and mounted onto to the plate support members 346, 348 of the holder 340 and the release lever 370 may be engaged, causing the plate gripper 344 to move (e.g., up) along the longitudinal axis of the arm 300 to engage a portion (e.g., a lower portion) of the locking plate 5 and drive another portion (e.g. an upper portion) of the locking plate 5 in the same direction against the associated plate gripper 342, so that the locking plate 5 is securely nested in the holder 340.

After the barrel assembly 2, 3 and pivoting plate 4 have been securely loaded and nested in the holder 240, and the locking plate 5 has been securely loaded and nested in the holder 340, the barrel assembly 2, 3 and pivoting plate 4 may be inserted in an interspinous space between a pair of spinous processes.

Figure 2B:
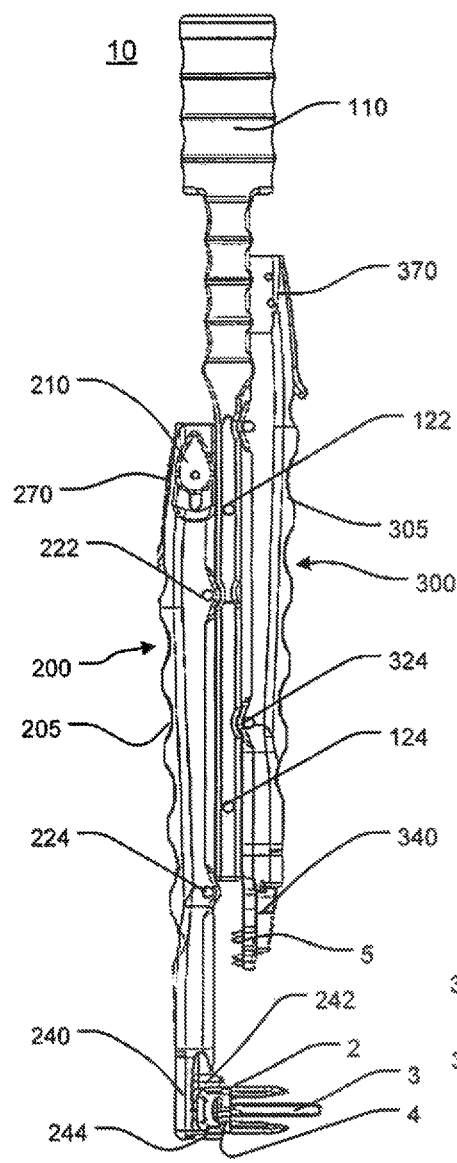
FIG. 2B shows a side view of the surgical device of FIG. 2A.
Figure 2C:
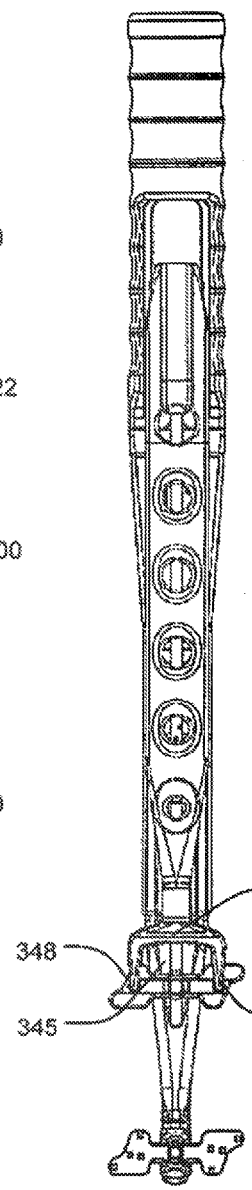
FIG. 2C shows a rear view of the surgical device of FIG. 2A.
Figure 2D:
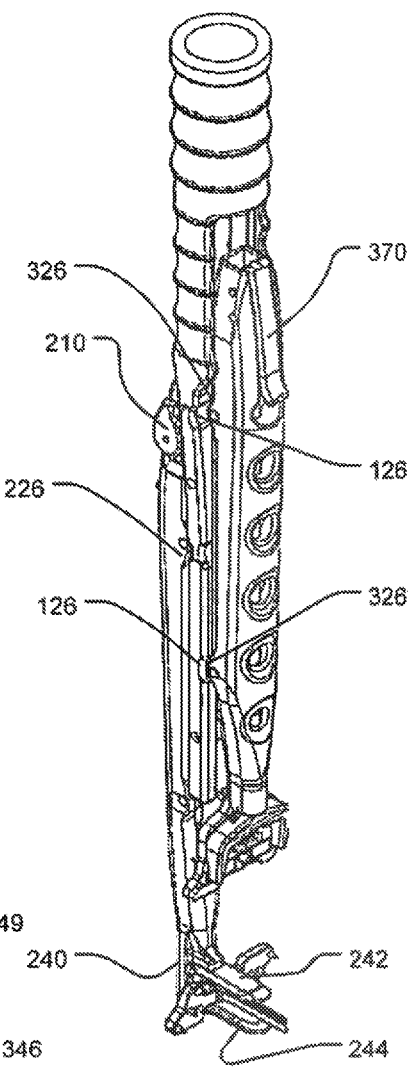
FIG. 2D shows a perspective side view of the surgical device of FIG. 2A.
Figure 3A:
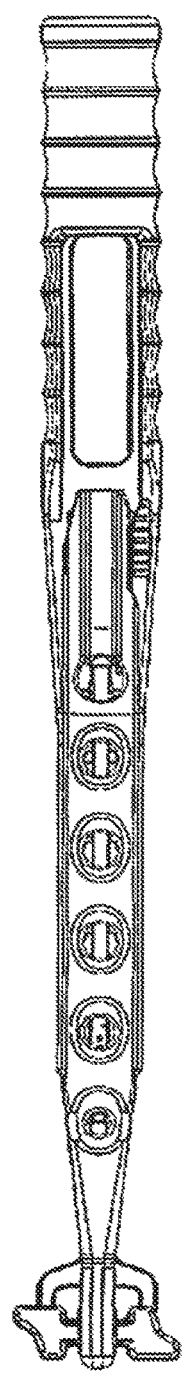
Figure 3B:
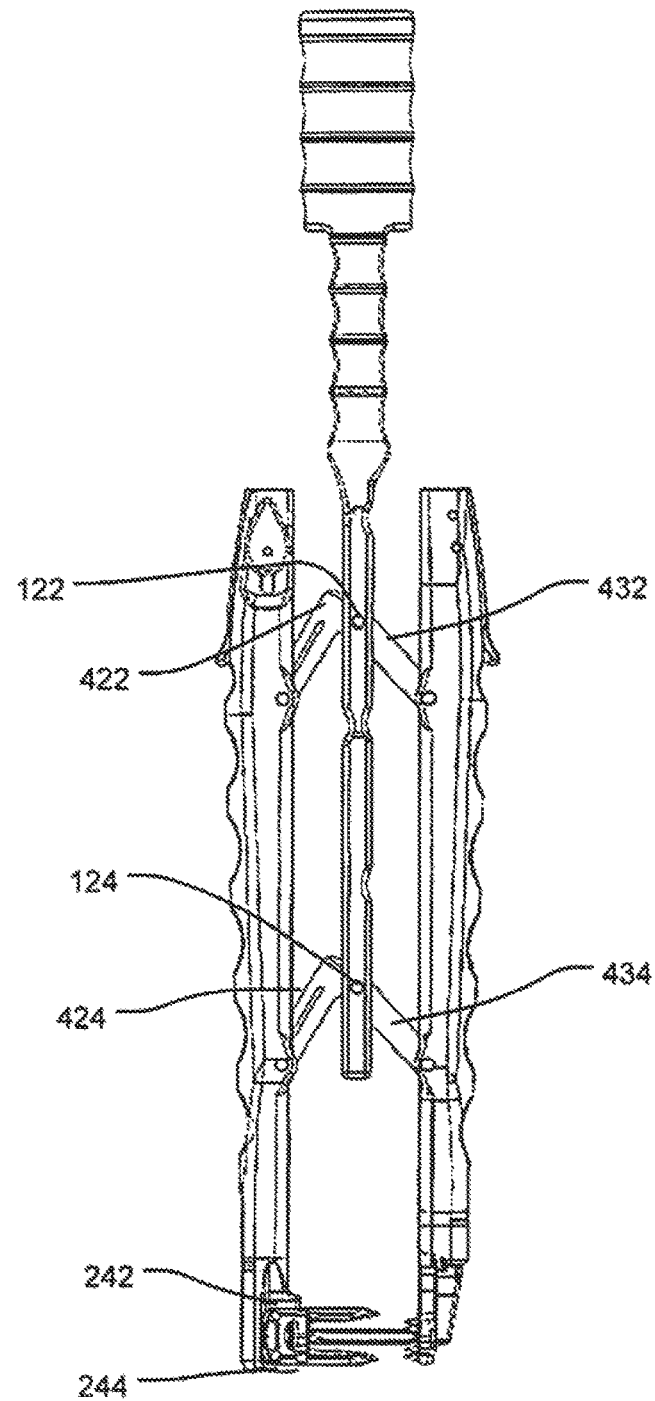

Referring to FIG. 2B, the arm 200 may be extended along its longitudinal axis to its fully extended length. The holder 240, including the nested barrel assembly 2, 3 and pivoting plate 4 may be inserted through an opening and positioned proximate an interspinous space that is to be treated. After proper alignment, the barrel assembly 2, 3 and pivoting plate 4 may be inserted into the interspinous space.

Referring to FIG. 3D, the arm 200 may be extended in a direction that is substantially perpendicular to its longitudinal axis with respect to the arm support portion 120. Simultaneously, or subsequently, the arm 300 may be extended along its longitudinal axis to its full extended length. The holder 340, including the lock plate 5 may be inserted through the opening and positioned in alignment with the barrel assembly 2, 3 and pivoting plate 4, as seen in FIG. 3D. The actuator 210 may be manipulated to cause the pockets 24 of the barrel body 2 to be squeezed toward each other, thereby causing the extensions 21, 22 to move away from each other, widening the mouth 23 opening of the barrel body 2, as discussed above, thereby allowing for the lock plate 5 to be squeezed into the mouth of the barrel 2 until it engages the upper and lower spinous processes surrounding the interspionous space that is being treated. The arms 200 and 300 may be squeezed toward each other, thereby driving the plates 4, 5 against the upper and lower spinous processes and firmly attaching the plates 4, 5 to the spinous processes. The actuator 210 may then be manipulated to close the mouth 23 of the barrel body 2, thereby engaging and locking the locking plate 5 into position with regard to the barrel assembly 2, 3, the pivoting plate 4, and the upper and lower spinous processes. The release levers 270, 370 may be disengaged (or released) to release the implant 1. After the implant 1 has been released, the arms 200, 300 may be expanded to allow the holders 240, 340 to clear the implant 1 and to be removed from the surgical area.

An implant 1 may be removed from a patient by repeating the foregoing steps in a reverse order.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A surgical system comprising:
   an implant comprising:
      a first plate;
      a second plate; and
      a barrel assembly;
   an insertion instrument for delivering the implant into a patient, the insertion instrument comprising:
      a handle portion;
      an arm support portion attached to the handle portion;
      a first arm extending from the arm support, wherein the first arm is configured to retain the first plate and the barrel assembly; and
      a second arm extending from the arm support, wherein the second arm is configured to retain the second plate,
      wherein the first arm moves independently from the second arm and is configured to move laterally and longitudinally.

2. The surgical system of claim 1, wherein the first plate comprises a pivoting plate and the second plate comprises a locking plate.

3. The surgical system of claim 1, wherein the barrel assembly comprises a barrel body and an integrated central ratcheting rod.

4. The surgical system of claim 1, wherein the barrel assembly comprises a central ratcheting rod positioned between the pair of extensions.

5. The surgical system of claim 1, wherein each of the first arm and the second arm are moveable along a longitudinal axis of the arm support.

6. The surgical system of claim 1, wherein the barrel assembly comprises a pair of extensions that form a mouth.

7. The surgical system of claim 1, wherein the arm support portion comprises one or more cavities.

8. The surgical system of claim 1, wherein the first arm comprises an actuator, an arm body and a holder.

9. The surgical system of claim 8, wherein the actuator comprises a dial that allows for the first arm to move along a longitudinal axis of the first arm.

10. A surgical system comprising:
   an implant comprising:
      a first plate;
      a second plate; and
      a barrel assembly,
      wherein the barrel assembly comprises a pair of extensions and a rod positioned between the pair of extensions;
   an insertion instrument for delivering the implant into a patient, the insertion instrument comprising:
      an arm support portion;
      a first arm extending from the arm support, wherein the first arm is configured to retain the first plate and the barrel assembly; and
      a second arm extending from the arm support, wherein the second arm is configured to retain the second plate
      wherein the first arm moves independently from the second arm and is configured to move laterally and longitudinally.

11. The surgical system of claim 10, wherein the first arm is configured to move along a longitudinal axis of the first arm and the second arm is configured to move along a longitudinal axis of the second arm.

12. The surgical system of claim 10, wherein the first arm comprises an actuator for moving the first arm along a longitudinal axis of the first arm.

13. The surgical system of claim 12, wherein the actuator comprises a dial attached to a cam.

14. The surgical system of claim 10, wherein the first arm comprises an actuator and a gripper.

15. The surgical system of claim 14, wherein the first arm further comprises a release lever.

16. The surgical system of claim 10, wherein the first plate is configured to engage a first side of a spinous process of the patient and the second plate is configured to engage a second side of the spinous process of the patient.

17. The surgical system of claim 10, wherein the rod comprises a ratcheting rod.

18. The surgical system of claim 17, wherein the first arm and second arm move along their respective longitudinal axes.

* * * * *